(12) United States Patent
Li et al.

(10) Patent No.: US 11,796,525 B2
(45) Date of Patent: Oct. 24, 2023

(54) INSTRUMENT AND METHOD FOR SIMULTANEOUSLY TESTING MOLECULAR WEIGHT DISTRIBUTION AND ORGANIC NITROGEN LEVEL OF WATER SAMPLE

(71) Applicant: TONGJI UNIVERSITY, Shanghai (CN)

(72) Inventors: Lei Li, Shanghai (CN); Wenjun Zhang, Shanghai (CN); Shichong Wang, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 581 days.

(21) Appl. No.: 17/056,425

(22) PCT Filed: Aug. 29, 2018

(86) PCT No.: PCT/CN2018/102945
§ 371 (c)(1),
(2) Date: Nov. 18, 2020

(87) PCT Pub. No.: WO2019/218530
PCT Pub. Date: Nov. 21, 2019

(65) Prior Publication Data
US 2021/0208116 A1  Jul. 8, 2021

(30) Foreign Application Priority Data
May 18, 2018  (CN) .......................... 201810480696.0

(51) Int. Cl.
  *G01N 33/18*  (2006.01)
  *G01N 21/78*  (2006.01)
  (Continued)

(52) U.S. Cl.
  CPC .......... *G01N 33/182* (2013.01); *G01N 21/78* (2013.01); *G01N 30/14* (2013.01); *G01N 30/64* (2013.01);
  (Continued)

(58) Field of Classification Search
  CPC ...... G01N 33/182; G01N 21/78; G01N 30/14; G01N 30/64; G01N 30/88; G01N 33/1846; G01N 2030/645; G01N 2030/884
  (Continued)

(56) References Cited

U.S. PATENT DOCUMENTS

2004/0043499 A1*  3/2004  Lee-Alvarez ...... G01N 33/1826
                                                    422/68.1
2008/0220533 A1*  9/2008  Fujiyama ........... G01N 33/1846
                                                    422/82.02
(Continued)

FOREIGN PATENT DOCUMENTS

AT            509275 A1 *  7/2011 ............. G01N 33/24
CN         100541171 C *  9/2009
(Continued)

OTHER PUBLICATIONS

"International Search Report (Form PCT/ISA/210)" of PCT/CN2018/102945, dated Feb. 19, 2019, with English translation thereof, pp. 1-4.

*Primary Examiner* — Stephanie E Bloss
*Assistant Examiner* — Kevin C Butler
(74) *Attorney, Agent, or Firm* — JCIP GLOBAL INC.

(57) ABSTRACT

An instrument and a method for simultaneously testing a molecular weight distribution and an organic nitrogen level of a water sample are provided. The instrument comprises: a tail-end injection valve, a chromatographic column, a pressure relief valve, an acid-adding injection valve, an
(Continued)

oxygen-adding injection valve, a helical tube for an acid-oxygen reaction, a $CO_2$ remover, a UV digester, a second gas-water separator membrane, a buffer solution injection valve, a helical tube for a buffer solution reaction, a cadmium column, a chromogenic agent injection valve, a helical tube for a chromogenic agent reaction, and a UV detector, sequentially connected via a pipeline. The tail-end injection valve is for receiving a fluid phase and a sample. The second gas-water separator membrane is connected to an electrical conductivity-based CO2 detector. The UV detector and the electrical conductivity-based $CO_2$ detector are connected to a data processing computer.

10 Claims, 2 Drawing Sheets (51) Int. Cl.
*G01N 30/04* (2006.01)
*G01N 30/64* (2006.01)
*G01N 30/88* (2006.01)
*G01N 30/14* (2006.01)

(52) U.S. Cl.
CPC ......... *G01N 30/88* (2013.01); *G01N 33/1846* (2013.01); *G01N 2030/645* (2013.01); *G01N 2030/884* (2013.01)

(58) Field of Classification Search
USPC ........................................ 73/61.53
See application file for complete search history.

(56) References Cited

U.S. PATENT DOCUMENTS

| | | | | |
|---|---|---|---|---|
| 2012/0178175 A1* | 7/2012 | Crosman | ............... | G01N 27/06 422/69 |
| 2020/0173968 A1* | 6/2020 | Li | ............. | G01N 30/62 |
| 2021/0208116 A1* | 7/2021 | Li | ........... | G01N 33/182 |
| 2022/0146417 A1* | 5/2022 | Mao | ........... | G01N 33/18 |

FOREIGN PATENT DOCUMENTS

| | | | | |
|---|---|---|---|---|
| CN | 101655501 A | * | 2/2010 | |
| CN | 201662575 U | * | 12/2010 | |
| CN | 104730266 | | 6/2015 | |
| CN | 104730266 A | * | 6/2015 | |
| CN | 104730267 | | 6/2015 | |
| CN | 106124499 | | 11/2016 | |
| CN | 106124499 A | * | 11/2016 | |
| CN | 107024570 A | * | 8/2017 | |
| CN | 107655842 A | * | 2/2018 | ............... C02F 1/00 |
| CN | 108918746 | | 11/2018 | |
| CN | 108918746 A | * | 11/2018 | ............. G01N 21/78 |
| CN | 111707744 A | * | 9/2020 | |
| CN | 211955227 U | * | 11/2020 | |
| CN | 113189230 A | * | 7/2021 | ............. G01N 30/02 |
| EP | 1890141 A1 | * | 2/2008 | ......... G01N 33/1846 |
| EP | 2341339 A2 | * | 7/2011 | ............. G01N 33/24 |
| JP | H09281099 | | 10/1997 | |
| JP | H09281099 A | * | 10/1997 | ............. G01N 31/00 |
| WO | WO-2006126296 A1 | * | 11/2006 | ......... G01N 33/1846 |

* cited by examiner

INSTRUMENT AND METHOD FOR SIMULTANEOUSLY TESTING MOLECULAR WEIGHT DISTRIBUTION AND ORGANIC NITROGEN LEVEL OF WATER SAMPLE

CROSS-REFERENCE TO RELATED APPLICATION

This application is a 371 of international application of PCT application serial no. PCT/CN2018/102945, filed on Aug. 29, 2018, which claims the priority benefit of China application no. 201810480696.0, filed on May 18, 2018. The entirety of each of the above mentioned patent applications is hereby incorporated by reference herein and made a part of this specification.

TECHNICAL FIELD

The invention relates to environmental detection's technical field, particularly to an instrument and a method for simultaneously testing molecular weight distribution and organic nitrogen in water samples.

BACKGROUND

Due to the vast land area, the total amount of freshwater resources in China is relatively high, ranking fourth globally, accounting for 6% of the world's total amount of water resources in the world. However, because of the large population, the per capita share of freshwater resources is only 121st globally, China is still a severe water shortage country. Although the per capita possession of freshwater resources is seriously insufficient, various kinds of environmental water pollution still appear in many parts of the country, such as the abuse of organic pesticides, personal nursing supplies, washing powder containing phosphorus, the discharge of industrial wastewater without treatment and accidental discharge, agriculture, animal husbandry sewage into the water body and so on. These behaviors are further polluting our scarce water resources. The control of water environment pollution needs to "prevent" and "control" go hand in hand. First of all, it is necessary to start from the source and avoid the polluted water discharged directly into the water body without treatment. Secondly, while reducing the discharge of pollutants into the water body, we also need to carry out comprehensive and effective treatment of the polluted water body.

How to utilize the right method in controlling water environment pollution has always been the focus of water pollution control. The methods such as advanced oxidation, the membrane separation, and other treatment processes have been proposed. Although these methods can effectively degrade the pollutants in the polluted water to a lower level, there will inevitably be a large dosing and the harmful effect, leading to secondary pollution caused by excessive reagent and uneconomical treatment. The key to solving these problems is to master more comprehensive and accurate water quality data before treatment and have a thorough understanding of pollution. The most comprehensive and accurate water quality data can provide the basis for improving water treatment technology to put forward a more accurate treatment scheme.

The collection of water quality data of the polluted water body depends on better water quality detection technology. Traditionally, water samples are obtained from polluted water bodies and transported to the laboratory. A series of water quality analysis instruments can characterize polluted water bodies' quality to obtain water quality data. However, such water quality testing has the following shortcomings:

1. In the detection process, the acquisition of different kinds of water quality data is separate, so the pertinence of water quality data is reduced. An example is given to show that the dissolved organic nitrogen (DON) content cannot be analyzed at the same time when the total organic carbon (TOC) concentration in the water sample is analyzed. The TOC concentration and the DON concentration of the water sample are independent at this time, and the water quality can not be characterized more specifically. For example, even after adding the total nitrogen (TN) module, the detection of TOC and TN concentrations by Shimadzu's TOC analyzer is still independent, and it is still unable to detect DON concentration synchronously. Although the series of multi-parameter water quality analyzers of HACH Company in the United States can detect the parameters such as TN, ammonia nitrogen, the instrument combines several independent measuring modules. Unlike the detection instrument mentioned above, the invention can realize the synchronous detection of TOC concentration and DON concentration using primary oxidation, thereby further improving the pertinence of water quality data and realizing the full amplitude multi-dimensional detection of water quality.

2. The DON concentration is difficult to detect accurately, but it is essential to the drinking water supply's safety. For example, to ensure the concentration of disinfection by-products in the effluent of water plants, mostly the current new nitrogen-containing disinfection by-products, it is necessary to strictly control the number of disinfectants according to the different influent quality, because one of the sources of nitrogen-containing disinfection by-products is DON. For controlling the amount of nitrogen disinfection by-products in the effluent, it is crucial to monitor the concentration of DON in influent. Zhang Liang, Harbin University of Technology, discussed the shortcomings of DON concentration detection methods at domestic and abroad and put forward the method of DON concentration detection by electricity-driven dialysis pretreatment. The accuracy of this method for DON concentration detection is improved. The shortcomings are the common problems of most DON concentration detection methods, such as the long detection time, the low detection efficiency, and the complex operation in the detection process. There are two methods commonly used in laboratory detection of DON: TN minus total inorganic nitrogen and Kjeldahl nitrogen minus ammonia nitrogen. The method needs many detection times, so the accumulated systematic error dramatically influences the results. At present, most of instruments can only detect the concentration of TN, ammonia nitrogen. For example, the TN analyzer of WTW in Germany is a combination of three modules. The instrument also uses the above method for the detection of DON concentration. Unlike the detection instrument mentioned above, the invention can realize DON concentration using the separation of a chromatographic column, which is convenient, fast, and accurate. It makes up for the shortcomings of the current DON concentration detection methods.

The lack of water quality detection mentioned above brings difficulties in collecting water quality data of polluted water bodies, so it cannot provide more accurate treatment measures. At present, it is urgent to detect the TOC concentration and DON concentration of different pollutants in different molecular weight ranges in the control of water environment pollution. Patent No. 2015101472555 publishes an instrument and method that can detect TOC, TN and total phosphorus concentrations synchronously. Although this instrument and method can realize synchronous detection of three indexes, the detection of TN concentration is used direct ultraviolet spectrophotometry, that is, DON was oxidized to produce nitrate nitrogen and then irradiated directly with 220 nm UV lamp to detect nitrate nitrogen by absorbance, to convert the concentration of DON. However, this method's detection limit is high, and the UV signal is interfered with other impurity examples, so the accuracy of the experimental results cannot be guaranteed. Also, the above patent cannot realize the synchronous detection of DON concentration. Another patent, 201610712720X, proposed an instrument for simultaneous detection of TN, total phosphorus, TOC by UV digestion. The patent cannot realize the synchronous detection of DON concentration.

In a word, there is no instrument or convenient and accurate method for simultaneous detection of TOC concentration and DON concentration of different pollutants in different molecular weight ranges at domestic and abroad.

SUMMARY

The invention is dedicated to solving the shortcomings of the pollution water quality detection mentioned above. It provides the instrument and method for simultaneously detecting the molecular weight distribution and organic nitrogen of water samples. The invention can simultaneously detect the TOC concentration and DON concentration of the water sample components measured in different molecular weight distribution ranges. According to the existing molecular weight distribution map, the qualitative and quantitative detection of different molecular weight components was realized. The measured data can be displayed and stored in the form of a chromatogram on the computer. They can be summarized on a chromatogram by the relevant drawing software for forward analysis.

The purpose of the invention can be realized through the following technical proposals:

An instrument for simultaneously testing the molecular weight distribution and organic nitrogen of water samples, including tail-end injection valve, chromatographic column, pressure relief valve, acid-adding injection valve, oxygen-adding injection valve, helical tube for an acid-oxygen reaction, carbon dioxide ($CO_2$) remover, ultraviolet digester, the second gas-water separation membrane, the buffer solution injection valve, the helical tube for a buffer solution reaction, the cadmium column, the chromogenic agent injection valve, the helical tube for a chromogenic agent reaction and the ultraviolet detector; all these devices are connected in sequence by pipelines. The tail-end injection valve is used to receive the fluid phase and the sample. The second gas-water separation membrane is connected to an electrical conductivity-based $CO_2$ detector. The ultraviolet detector and the electrical conductivity-based $CO_2$ detector are both connected to a computer for data processing.

The tail-end injection valve is connected with a sampling pump and a sample bottle, and it is also connected with a fluid phase infusion pump and a fluid phase reagent bottle.

The acid-adding injection valve is connected with an acid injection pump and an acid bottle.

The oxygen-adding injection valve is connected with an oxygen liquid injection pump and an oxygen liquid bottle.

The buffer solution injection valve is connected with the buffer solution injection pump and the buffer solution reagent bottle.

The chromogenic agent injection valve is connected with the chromogenic agent injection pump and the chromogenic agent reagent bottle.

The $CO_2$ remover includes a first gas-water separation membrane, a gas collecting coil, a purge pump and a diaphragm. The first gas-water separation membrane, the gas collecting coil and the diaphragm are connected in sequence. The first gas-water separation membrane is connected to the acid-oxygen reaction spiral pipe through a pipeline. The diaphragm is connected with the transparent quartz spiral tube through the outlet vent pipe and pipeline. The blow-off pump is connected to the gas collecting coil. The first gas-water separation membrane function is to separate the $CO_2$ produced by inorganic carbonation from the liquid components and then enter the gas collecting coil. The first gas-water separation membrane is preferably a polydimethylsiloxane membrane, an oxygen-rich membrane with a stable structure and a good separation effect on $CO_2$. The diaphragm purpose is to isolate the air's $CO_2$ and prevent it from entering the tested components. The blow-off pump's function is to provide blow-off power and blow out the gas collecting coil's $CO_2$. The blow-off pump is a micro pneumatic diaphragm pump, which is small in size, can effectively provide blowing power and is cheap.

The ultraviolet digester includes a heating wire, a transparent quartz spiral tube and an ultraviolet lamp. The transparent quartz spiral tube is connected between the diaphragm and the second gas-water separation membrane through a pipeline. The ultraviolet lamp is located above the transparent quartz spiral tube. The heating wire is located under the transparent quartz spiral tube.

The second water-gas separation membrane is connected between the UV digestion apparatus and buffer solution injection valve. The second gas-water separation membrane connected with electrical conductivity-based $CO_2$ detector, which is used for separating $CO_2$ produced in UV digestion apparatus. The rest of the sample enter into the buffer solution injection valve, and then enter the UV detector. The second gas water separation membrane optimization is polydimethylsiloxane membrane, belongs to the oxygen-enriched membrane. It has a good separation effect on $CO_2$ and has a stable structure.

The electrical conductivity-based $CO_2$ detector comprises an ultra-pure water tank and an ultra-pure water pump connected sequentially. The sample oxidized by a UV digestion device pass through a gas-water separation membrane. The $CO_2$ was separated and dissolved in ultra-pure water driven by an ultra-pure water pump and purified by ion purification resin. Then, it was passed into the conductivity cell. The amount of $CO_2$ was measured by detecting the change of liquid conductivity in the conductivity cell, and a specific conversion relationship characterized the concentration of TOC.

As the best choice, the ultra-pure water is made by Milli-Q ultra-pure water instrument, the resistance is 18.2 m$\Omega$·cm, the ultra-pure water pump is micro-infusion pump, and the conductivity electrode flow cell with measuring range of 0.01 μs/cm-300 μs/cm, resolution of 0.01 μs/cm is selected.

The chromatographic column is located in a chromatographic column temperature box.

The UV detector is connected with the waste liquid bucket.

The UV detector is connected to a computer for data processing through a UV detector data line. The electrical conductivity-based $CO_2$ detector is connected to a computer for data processing through an electrical conductivity-based $CO_2$ detector data line.

The simultaneous detection of molecular weight distribution and organic nitrogen in water samples using the above instruments includes the following steps.

The sample is collected into the pipeline by the sample pump, mixed with the flow transported by the infusion pump through the tail-end injection valve, and then separated by the liquid phase column in the chromatographic column temperature box. The sample flow components out in turn according to the molecular weight, and then the pressure is reduced to about one atmospheric pressure by the pressure relief valve. The different molecular weight components of the separated sample pass through the acid-adding injection valve and the oxygen-adding injection valve. Meanwhile, the acid injection pump of the acid pipeline will inject acid into the acid-adding injection valve. According to the set quantity, the oxygen injection pump of the oxygen liquid pipeline will inject the oxygen solution into the oxygen-adding injection valve. After the tested components, fluid phase, acid solution and oxygen solution are fully reacted in the acid-oxygen reaction spiral tube; inorganic carbon in the component to be tested will be acidified by the acid solution to produce $CO_2$, which is blown off into the air through the back remover of $CO_2$. The components to be tested removed from inorganic carbon reached in the UV decomposer through the pipeline. Under UV lamp irradiation and heating conditions, TOC will be oxidized to $CO_2$ and DON will be oxidized to nitrate nitrogen. The oxidized sample passed through a gas-liquid separation membrane to separate the generated $CO_2$ into the electrical conductivity-based $CO_2$ detector. The detector detects the amount of $CO_2$, and a specific conversion relationship characterizes the concentration of TOC. After that, the remaining components without TOC will add to a buffer solution through the injection valve. Then after the reduction of the cadmium column, nitrate nitrogen is reduced to nitrite nitrogen. The reagent is added through the color reagent injection valve, and the mixing reaction is carried out in the spiral tube of the reagent reaction. Finally, the amount of nitrate-nitrogen is detected at 540 nm in the UV detector. A specific conversion relationship characterizes the concentration of DON. After the detection, the waste liquid of the UV detector and electrical conductivity-based $CO_2$ detector is discharged into the waste liquid bucket through the waste liquid tube.

The chromatographic column is the size exclusion chromatographic column, The effective range of molecular weight discrimination can be set according to the user's needs and can generally be selected as 500×800000 Da.

The flow is selected according to the requirements of the chromatographic column. It is generally selected as a phosphate buffer solution of which the ion strength is 0.1-0.4 M, and the pH is 6.8±0.2.

The infusion pump's flow rate shall ensure that each chromatographic peak is sharp, easy to distinguish. And within the allowable flow rate of the chromatographic column. The general option is 0.4-1.0 mL/min. The infusion pump pressure should be within the allowable pressure range of the chromatographic column, which is generally selected as 1.8±0.2 MPA.

The chromatographic column's column temperature should be adjusted according to the peak condition of the sample in the oven, which has a heating wire. On the one hand, it is necessary to ensure that each chromatographic peak's width is narrow. On the other hand, it should be within the allowable temperature range of the chromatographic column. The chromatographic peak's general peak width is about 4-10 min, and the temperature is generally set at 30-60° C.

The sample pump shall collect the samples into the pipeline and mix them with the flow through the tail-end injection valve.

The sample pump adopts a microinjection pump. The pump's working pressure should be higher than 1500 psi, and the highest precision should be less than 0.1%. It adopts the pulse-free and uniform transportation, and the injection volume from very small to very large can be accurately distributed. The sampling volume should ensure that chromatography's peak is sharp and easy to distinguish and can be selected according to the separation effect of the chromatographic column. The general setting is 50-500 µL.

The acid bottle is used for filling acid liquid, and the acid solution should be selected according to the sample. It is necessary to ensure that all inorganic carbon is acidified to $CO_2$. The available option is 15%-30% phosphate.

The oxygen liquid bottle is used for loading the oxygen liquid. According to the sample, the oxygen solution should be selected to ensure all the TOC can be oxidized to $CO_2$. The available option is 10%-20% ammonium persulfate.

The acid injection pump and the oxygen injection pump should inject acid and oxygen into the main flow path according to a specific flow rate and will not affect the flow rate and pressure of the main flow path. The best choice is the microinjection pump, the working pressure higher than 1500 psi, the highest precision less than 0.1% and pulse-free transportation. The injection volume can be accurately distributed from very small to very large, and an injection valve connects the acidizing and oxidizing pipeline and the sample pipeline. The acid oxygen injection pump flow rate should ensure the excess of acid and oxygen solution, which can be selected according to the concentration of the sample and acid oxygen solution. The general choice is 1.0-4.0 µL/min.

The tail-end injection valve, acid-adding injection valve, oxygen-adding injection valve, buffer solution injection valve, and chromogenic agent injection valve can stably add one liquid to another liquid slowly and stably for mixing and Will not produce back suction. Preferably: an injection valve with a shut-off plate and a buffer pad. The shut-off plate prevents the liquid from flowing back and sucking, and the buffer pad helps to inject the liquid into another liquid stably and slowly.

The acid-oxygen reaction spiral tube is arranged between the UV decomposer and the oxygen-adding injection valve to ensure that the inorganic carbon is fully acidified into $CO_2$. It is preferred that the spiral steel PEEK tube is stain. On the one hand, the cost is reduced; on the other hand, stainless steel PEEK tube can effectively prevent chemical corrosion and ensure that the separated components will not be remixed.

The buffer solution reagent bottle is used for loading buffer solution. The buffer solution adopts an ammonium chloride buffer solution, dissolved in 800 mL water by 85 g ammonium chloride and 1 g disodium ethylenediaminetetraacetic acid dihydrate. It is mixed with 1000 mL at constant volume. The pH value of the solution is 8.5.

100 mL phosphate is dissolved in 600 mL water, then 40 g sulfonamide and 1 g N-ethylenediamine are added, diluted to 1000 mL with water, and the phosphate is selected and analyzed.

The purpose of the cadmium column is to reduce the oxidized nitrate nitrogen to nitrite nitrogen. The reduction efficiency should be higher than 98%. The filling of the cadmium column should be convenient and not easy to damage.

The buffer solution and the color rendering reagent reaction spiral tube are preferably made of stainless-steel PEEK tubes. On the one hand, the cost is reduced; on the other hand, stainless steel PEEK tube can effectively prevent chemical corrosion and ensure that the separated components will not be remixed.

The amount of the buffer solution shall be determined according to the actual water sample. The flow rate of the chromogenic injection pump shall ensure that an excessive amount of chromogenic agent. The general option is 1.0-4.0 µL/min.

The UV digester comprises a transparent quartz reactive spiral tube, a UV lamp and a heating filament. The transparent quartz reactive helical tube provides enough reaction space. Under the condition of UV lamp irradiation and heating, the persulfate produced by the oxidant fully oxidizes the components to be tested. The UV lamp's wavelength is 190 nm, and the heating temperature is (95±2° C.).

The UV detector meets the requirements of the online detection of absorbance changes. It is equipped with a circulating sample pool, and the results are stored and output to a computer for further analysis. Preferably, the UV detector has a PEEK pipe joint, which can be detected online and can automatically draw the chromatogram UV detector by software.

The instrument's material internal sample line is stainless steel peek pipe to avoid sample corrosion. The primary flow rate is the same as the one of the fluid phase, which can be selected as 0.4~1.0 mL/min. The pressure before the liquid chromatography column is 1.8±0.2 MPa. The pressure through the pressure relief valve is 1 bar after the liquid chromatography column, and the flow state is free to flow.

The invention can simultaneously detect the TOC concentration and DON concentration of the water sample components to be measured in different molecular weight distribution ranges. The specific detection principle is:

The size exclusion chromatography column separates the samples, and the sample components in the effluent are arranged according to the size of the selected chromatographic column's separation range. The TOC concentration and DON concentration, which are the two most common water quality parameters in different molecular weight distribution ranges, are measured. The invention uses the principle that different molecular weight components in the water sample separated by size exclusion chromatography flow out according to the molecular weight. Combined with the detection of TOC concentration in the invention, it can accurately understand the different molecular weight distribution and determine the TOC concentration in different molecular weight distribution ranges. According to the repeated experiments on many standard samples containing nitrogen, the results are as follows: Within a specific residence time, the outflow column is DON. Combined with the detection of DON by the invention, the measurement of DON in the water sample is tested conveniently, efficiently and accurately.

That is to say, the invention can provide synchronous detection of TOC concentration and DON concentration of components of water samples to be measured in different molecular weight distribution ranges. The analysis time is significantly shortened, and more importantly, the invention can realize the synchronous collection of polluted water quality data in a complete sense.

The technical route of the invention is:

The samples are transmitted by the sampling pump, reached the pipeline, and injected into the fluid phase pipeline by the tail-end injection valve. The fluid phase in the fluid phase reagent bottle is transmitted to the main flow path under the action of the fluid phase infusion pump and mixed with the sample after reaching the end of the injection valve. The fluid phase carries the sample and is separated by a chromatographic column in a column. After separation by chromatographic column, the sample to be measured flows out according to its components' molecular weight in turn. The pressure is reduced to atmospheric pressure, and the flow pattern is the free outflow through the pressure reduction valve. The components to be tested then arrive at the acid-adding injection valve and the oxygen-adding injection valve in the mainstream road, mixed with the acid and oxygen transferred by the liquid injection pump and the oxygen injection pump and further reached the spiral tube of the acid-oxygen reaction. In the fluid phase, the components to be measured, the acid solution and the oxygen solution, are thoroughly mixed in the acid-oxygen reaction's spiral.

In the spiral of acid-oxygen reaction, inorganic carbon is completely acidified to $CO_2$ (reaction 1).

$$2H^+ + CO_3^{2-} \rightarrow CO_2 + H_2O \tag{1}$$

The inorganic carbon in the component to be tested is acidified by acid solution. The resulting $CO_2$ is mixed in the pipeline, entered into the $CO_2$ remover, and then separated from the liquid phase and discharged into the air. The structure of the $CO_2$ remover is as mentioned above: the resulting $CO_2$ is immediately separated from the liquid phase by the first gas-water separation membrane, enters the gas collecting coil, transmits through the blow-off pump, and blows the $CO_2$ into the air after blowing through the diaphragm. The $CO_2$ in the air is blocked by the diaphragm and does not enter the liquid phase.

The remaining components to be tested and the fluid phase of inorganic carbon were removed and entered the UV decomposer. The UV digester structure is described as above: the transparent quartz reaction spiral tube provides the reaction space in which the components to be tested. In the fluid phase, the oxygen solution and the acid are filled with a mixed spiral advance. Under the UV lamp's irradiation and the heating condition of electric heating wire, the TOC is oxidized to $CO_2$. The DON is oxidized to nitrate ion (reaction 2,3).

$$\text{TOC} \xrightarrow{S_2O_8^{2-},\ UV,\ Heat} CO_2 + H_2O \tag{2}$$

$$\text{DON} \xrightarrow{S_2O_8^{2-},\ UV,\ Heat} NO_3^{2-} + H_2O \tag{3}$$

At this time, $CO_2$ produced by TOC oxidation enters into the second gas-water separation membrane, separated from the liquid phase and enters into the electrical conductivity-based $CO_2$ detector. The structure of the electrical conductivity-based $CO_2$ detector is as described above. The separated $CO_2$ enters the electrical conductivity-based $CO_2$ detector from another flow path and is dissolved in the ultrapure water pipeline. The ultrapure water is driven by an ultrapure water pump and drawn from the ultrapure water tank. After dissolving $CO_2$, it enters into the conductive cell. The change of conductance detects the $CO_2$ content and then shows the TOC concentration.

The organic carbon-removed components reach the buffer solution injection valve and are mixed with the buffer solution injection pump's buffer solution. The mixed solution enters the helical tube for a buffer solution reaction for further mixing and then enters the cadmium column to reduce the nitrate-nitrogen produced by oxidation to nitrite nitrogen. Subsequently, the liquid stream is mixed with the chromogenic agent delivered by the chromogenic agent injection pump at the chromogenic agent injection valve and further reacts in the chromogenic agent reaction spiral tube. In the presence of an acidic medium, nitrite nitrogen undergoes a diazotization reaction with sulfonamides and then couples with naphthalene ethylenediamine hydrochloride to produce a purple-red substance.

Finally, the reaction solution enters the ultraviolet detector, and the nitrite nitrogen is used to generate absorption under ultraviolet light with a wavelength of 540 nm. The absorption amount conforms to Beer's law. After the photoelectric sensor obtains the signal, the amount of nitrite nitrogen is obtained after processing, which further characterizes DON concentration.

The wastewater at the outlet of the conductivity cell and the wastewater at the ultraviolet detector outlet are combined and collected into a waste liquid bucket. The data of the conductivity cell and the UV detector are respectively sent to the computer through the data transmission line for further storage and processing.

The outlet wastewater is collected into a waste liquid bucket after confluence. The ultraviolet detector is connected to the computer for data processing through the ultraviolet detector data line. The conductivity detector is connected to the computer for data processing through the conductance detector data line. The computer performs further storage and processing.

Compared with the existing technology, the technical features and advantages of the present invention are as follows:

1. Synchronization. The instrument can simultaneously qualitatively detect the types of components in the polluted water samples in different molecular weight distribution intervals and the organic carbon and organic nitrogen concentrations of the components in the different molecular weight distribution intervals that are simultaneously and quantitatively detected.
2. Comprehensiveness. The data obtained by the instrument has improved the detection mode that only had one data point per sample in the past and achieved a breakthrough in sample data from point to surface.
3. Pertinence. This instrument separates the sample to be tested through a chromatographic column. It then detects the organic carbon and organic nitrogen concentrations of pollutant components in different molecular weight distribution ranges. Water quality data is more pertinent and has important supporting significance for future research on nitrogen-containing disinfection by-products.
4. Accuracy. Compared with the traditional difference method, detecting the concentration of organic nitrogen proposed by this instrument has dramatically improved accuracy.
5. Simplicity. The method for detecting organic nitrogen concentration proposed by this instrument is simpler and more automated than common methods such as the dialysis membrane method, ion exchange column method, pre-concentration method, and catalytic reduction method. It improves the efficiency of water quality detection.

Reference numerals in the figure: 1—fluid phase reagent bottle; 2—fluid phase infusion pump; 3—tail—end injection valve; 4—sampling pump; 5—sample bottle; 6—chromatographic column; 7—column thermostat; 8—pressure relief valve; 9—acid—adding injection valve; 10—acid injection pump; 11—acid bottle; 12—oxygen—adding injection valve; 13—oxygen injection pump; 14—oxygen bottle; 15—helical tube for an acid—oxygen reaction; 16—UV digester; 17—buffer solution syringe pump; 18—buffer solution reagent bottle; 19—buffer solution injection valve; 20—helical tube for a buffer solution reaction; 21—cadmium column; 22—color reagent injection Valve; 23—chromogenic reagent injection pump; 24—chromogenic reagent bottle; 25—chromogenic reagent reaction spiral tube; 26—UV detector; 27—Waste liquid barrel; 28—computer; 29—heating wire; 30—transparent quartz spiral tube; 31—UV lamp; 32—$CO_2$ remover; 33—second gas—water separation membrane; 34—electrical conductivity—based $CO_2$ detector; 35—ultra pure water tank; 36—ultra pure water pump; 37—conductivity cell; 38—first gas—water separation membrane; 39—gas collecting coil; 40—purge pump; 41—diaphragm; 42—outlet vent pipe; 43—ultraviolet detector data line; 44—electrical conductivity—based $CO_2$ detector data line.

DETAILED DESCRIPTION

Figure 1:
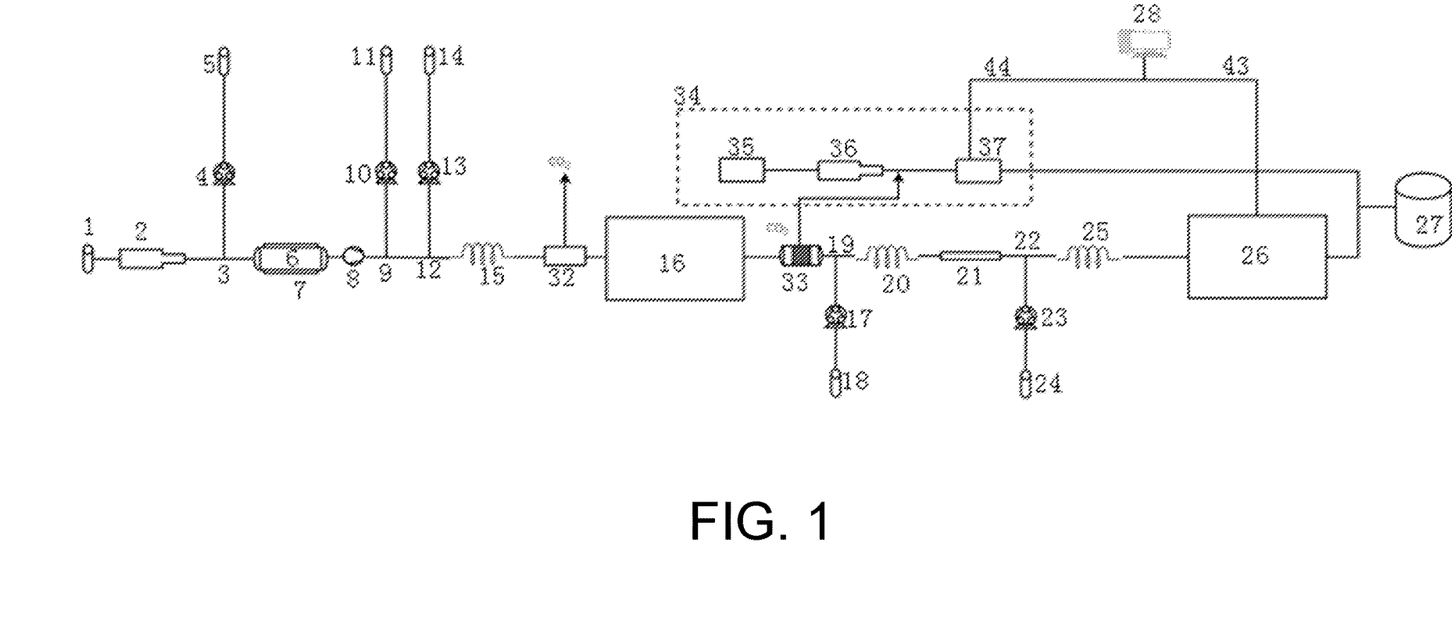
FIG. 1 is a schematic diagram of the instrument structure.

As shown in FIG. 1, an instrument for simultaneously testing the molecular weight distribution and organic nitrogen of water samples, including tail-end injection valve 3, chromatographic column 6, pressure relief valve 8, acid-adding injection valve 9, oxygen-adding injection valve 12, helical tube for an acid-oxygen reaction 15, carbon dioxide ($CO_2$) remover 32, ultraviolet digester 16, the second gas-water separation membrane 33, the buffer solution injection valve 19, the helical tube for a buffer solution reaction 20, the cadmium column 21, the chromogenic agent injection valve 22, the helical tube for a chromogenic agent reaction 25 and the ultraviolet detector 26; all these devices are connected in sequence by pipelines. The tail-end injection valve 3 is used to receive the fluid phase and the sample. The second gas-water separation membrane 33 is connected to an electrical conductivity-based $CO_2$ detector 34. The ultraviolet detector 26 and the electrical conductivity-based $CO_2$ detector 34 are both connected to a computer 28 for data processing.

The tail-end injection valve 3 is connected with a sampling pump 4 and a sample bottle 5, and it is also connected with a fluid phase infusion pump 2 and a fluid phase reagent bottle 1. The acid-adding injection valve 9 is connected with an acid injection pump 10 and an acid bottle 11. The oxygen-adding injection valve 12 is connected with an oxygen liquid injection pump 13 and an oxygen liquid bottle 14. The buffer solution injection valve 19 is connected with the buffer solution injection pump 17 and the buffer solution reagent bottle 18. The chromogenic agent injection valve 22 is connected with the chromogenic agent injection pump 23 and the chromogenic agent reagent bottle 24. The chromatographic column 6 is located in a chromatographic column temperature box 7. The UV detector 26 is connected with the waste liquid bucket 27. The UV detector 26 is connected to a computer 28 for data processing through a UV detector data line 43. The Electrical conductivity-based $CO_2$ detector 34 is connected to a computer 28 for data processing through a Electrical conductivity-based $CO_2$ detector data line 44.

Figure 2:
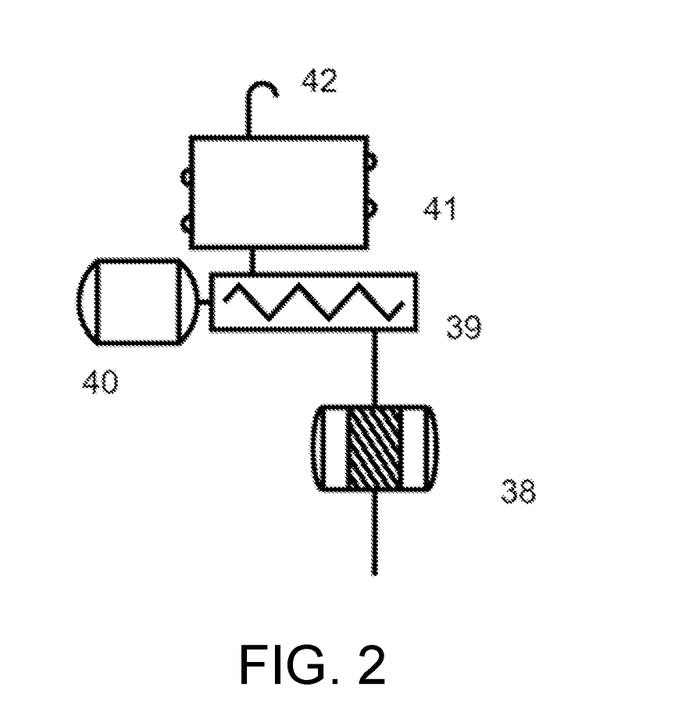
FIG. 2 is a schematic diagram of the structure of a $CO_2$ remover.

As shown in FIG. 2, the $CO_2$ remover 32 includes a first gas-water separation membrane 38, a gas collecting coil 39, a purge pump 40 and a diaphragm 41. The first gas-water separation membrane 38, the gas collecting coil 39 and the diaphragm 41 are connected in sequence. The first gas-water separation membrane 38 is connected to the acid-oxygen reaction spiral pipe 15 through a pipeline. The diaphragm 41 is connected with the transparent quartz spiral tube 30 through the outlet vent pipe 42 and pipeline. The blow-off pump 40 is connected to the gas collecting coil 39. The first gas-water separation membrane 38 function is to separate the $CO_2$ produced by inorganic carbonation from the liquid components and then enter the gas collecting coil. The first gas-water separation membrane 38 is preferably a polydimethylsiloxane membrane, an oxygen-rich membrane with a stable structure and a good separation effect on $CO_2$. The diaphragm 41 purpose is to isolate the air's $CO_2$ and prevent it from entering the tested components. The blow-off pump's 40 function is to provide blow-off power and blow out the gas collecting coil's $CO_2$. The blow-off pump 40 is a micro pneumatic diaphragm pump, which is small in size, can effectively provide blowing power and is cheap.

Figure 3:
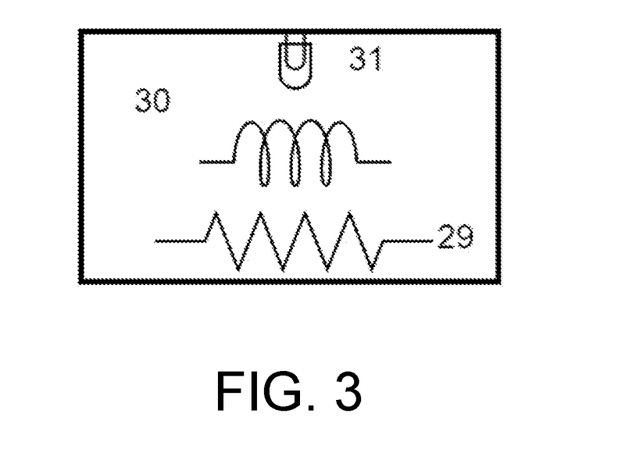
FIG. 3 is a schematic diagram of the structure of an ultraviolet digester.

As shown in FIG. 3, the ultraviolet digester 16 includes a heating wire 29, a transparent quartz spiral tube 30 and an ultraviolet lamp 31. The transparent quartz spiral tube 30 is connected between the diaphragm 41 and the second gas-water separation membrane 33 through a pipeline. The ultraviolet lamp 31 is located above the transparent quartz spiral tube 30. The heating wire 29 is located under the transparent quartz spiral tube.

The second water-gas separation membrane 33 is connected between the UV digestion apparatus 16 and buffer solution injection valve 19. The second gas-water separation membrane 33 connected with electrical conductivity-based $CO_2$ detector 34, which is used for separating $CO_2$ produced in UV digestion apparatus 16. The rest of the sample enter into the buffer solution injection valve 19, and then enter the UV detector. The second gas water separation membrane 33 optimization is polydimethylsiloxane membrane, belongs to the oxygen-enriched membrane. It has a good separation effect on $CO_2$ and has a stable structure.

The electrical conductivity-based $CO_2$ detector 34 comprises an ultra-pure water tank 35 and an ultra-pure water pump 36 connected sequentially. The sample oxidized by a UV digestion device 16 pass through a gas-water separation membrane 19. The $CO_2$ was separated and dissolved in ultra-pure water driven by an ultra-pure water pump 36 and purified by ion purification resin. Then, it was passed into the conductivity cell. The amount of $CO_2$ was measured by detecting the change of liquid conductivity in the conductivity cell, and a specific conversion relationship characterized the concentration of TOC.

As the best choice, the ultra-pure water is made by Milli-Q ultra-pure water instrument, the resistance is 18.2 mΩ·cm, the ultra-pure water pump 36 is micro-infusion pump, and the conductivity electrode flow cell with measuring range of 0.01 μs/cm-300 μs/cm, resolution of 0.01 μs/cm is selected.

The technical route of the invention is shown in FIG. 1:

The samples 5 are transmitted by the sampling pump 4, reached the pipeline, and injected into the fluid phase pipeline by the tail-end injection valve 3. The fluid phase in the fluid phase reagent bottle 1 is transmitted to the main flow path under the action of the fluid phase infusion pump 2 and mixed with the sample after reaching the tail-end injection valve 3. The fluid phase carries the sample and is separated by a chromatographic column 6 in a temperature box 7. After separation by chromatographic column 6, the sample to be measured flows out according to its components' molecular weight in turn. The pressure is reduced to atmospheric pressure, and the flow pattern is the free outflow through the pressure reduction valve 8. The components to be tested then arrive at the acid-adding injection valve 9 and the oxygen-adding injection valve 12 in the mainstream road, mixed with the acid and oxygen transferred by the liquid injection pump 10 and the oxygen injection pump 13 and further reached the spiral tube of the acid-oxygen reaction. In the fluid phase, the components to be measured, the acid solution and the oxygen solution, are thoroughly mixed in the acid-oxygen reaction's spiral 15.

In the spiral of acid-oxygen reaction spiral 15, inorganic carbon is completely acidified to $CO_2$ (reaction 1).

$$2H^+ + CO_3^{2-} \rightarrow CO_2 + H_2O \tag{1}$$

The inorganic carbon (IC) in the component to be tested is acidified by acid solution. The resulting $CO_2$ is mixed in the pipeline, entered into the $CO_2$ remover 16, and then separated from the liquid phase and discharged into the air. The structure of the $CO_2$ remover 16 is as mentioned above:

the resulting CO$_2$ is immediately separated from the liquid phase by the first gas-water separation membrane 38, enters the gas collecting coil 39, transmits through the blow-off pump 40, and blows the CO$_2$ into the air after blowing through the diaphragm 41. The CO$_2$ in the air is blocked by the diaphragm 41 and does not enter the liquid phase.

The remaining components to be tested and the fluid phase of inorganic carbon were removed and entered the UV digester 16. The UV digester 16 structure is described as above: the transparent quartz reaction spiral tube provides the reaction space in which the components to be tested. In the fluid phase, the oxygen solution and the acid are filled with a mixed spiral advance. Under the UV lamp's 31 irradiation and the heating condition of electric heating wire 29, the TOC is oxidized to CO$_2$. The DON is oxidized to nitrate ion (reaction 2, 3).

(2)

(3)

At this time, CO$_2$ produced by TOC oxidation enters into the second gas-water separation membrane 33, separated from the liquid phase and enters into the electrical conductivity-based CO$_2$ detector 34. The structure of the electrical conductivity-based CO$_2$ detector is shown in the dashed box of FIG. 1. The separated CO$_2$ enters the electrical conductivity-based CO$_2$ detector from another flow path and is dissolved in the ultrapure water pipeline. The ultrapure water is driven by an ultrapure water pump and drawn from the ultrapure water tank. After dissolving CO$_2$, it enters into the conductive cell. The change of conductance detects the CO$_2$ content and then shows the TOC concentration.

The organic carbon-removed components reach the buffer solution injection valve 19 and are mixed with the buffer solution injection pump's 17 buffer solution. The mixed solution enters the helical tube for a buffer solution reaction 20 for further mixing and then enters the cadmium column 21 to reduce the nitrate-nitrogen produced by oxidation to nitrite nitrogen. Subsequently, the liquid stream is mixed with the chromogenic agent delivered by the chromogenic agent injection pump 23 at the chromogenic agent injection valve 22 and further reacts in the chromogenic agent reaction spiral tube 25. In the presence of an acidic medium, nitrite nitrogen undergoes a diazotization reaction with sulfonamides and then couples with naphthalene ethylenediamine hydrochloride to produce a purple-red substance.

Finally, the reaction solution enters the ultraviolet detector 26, and the nitrite nitrogen is used to generate absorption under ultraviolet light with a wavelength of 540 nm. The absorption amount conforms to Beer's law. After the photoelectric sensor obtains the signal, the amount of nitrite nitrogen is obtained after processing, which further characterizes DON concentration.

The wastewater at the outlet of the conductivity cell 37 and the wastewater at the ultraviolet detector 26 outlet are combined and collected into a waste liquid bucket 27. The data of the conductivity cell 23 and the UV detector 33 are respectively sent to the computer 28 through the data transmission line 35 and 34 for further storage and processing.

The outlet wastewater is collected into a waste liquid bucket 27 after confluence. The ultraviolet detector 26 is connected to the computer 28 for data processing through the ultraviolet detector data line 43. The conductivity detector 34 is connected to the computer 28 for data processing through the conductance detector data line 44. The computer 28 performs further storage and processing.

The present invention will be described in detail regarding the drawings and specific embodiments.

Embodiment

Preparation:

Turn on the instrument and computer 28. The fluid phase is subjected to ultrasonic degassing treatment for 20 minutes to eliminate bubbles in the fluid phase. This operation can avoid interference with the test results. Pass the sample through a 0.45 μm PTFE membrane to remove particulate impurities and avoid clogging of the instrument. Set the temperature of the column oven. In the ultraviolet digester 16, the ultraviolet lamp's wavelength is set to 190 nm, and the heating temperature is set to 95° C. Turn on the ultraviolet detector 26, and set the detection wavelength to 540 nm. The ultrapure water pump 36 is turned on, and the ultrapure water in the CO$_2$ detector starts to flow. Empty the waste container 27.

Operation Steps:

After the preparation work is finished, turn on the fluid phase infusion pump 2, and set the flow rate and pressure. After the baseline is stable (1 to 2 hours), set the sampling volume of the sampling pump, the acid oxygen injection pump's flow rate, the buffer solution injection pump, and the chromogenic agent injection pump. Turn on the sampling pump 4, acid injection pump 10, oxygen injection pump 13, buffer solution injection pump 17, and chromogenic agent injection pump 23. Inject the sample into the fluid phase through the tail-end injection valve 3, inject the acid and oxygen into the fluid phase, and then wait for the test result.

The main chromatographic condition intervals of this embodiment are as follows:

| SEC column | Flow rate of fluid phase infusion pump (mL/min) | Volume of water sample | Temperature of column thermostat | Flow rate of acid/oxidant injection pump | Flow rate of buffer solution injection pump | Flow rate of color reagent injection Valve |
|---|---|---|---|---|---|---|
| TSkgel G5000PW$_{XL}$ and TSkgel G2500PW$_{XL}$ columns series | 0.4~1.0 | 50~100 | 40~60 | 2.0~4.0 | 2.0~4.0 | 2.0~4.0 |

The residence time of different molecular weight standard samples obtained from TOC chromatographic peaks is as follows:

| MW | 210 | 4300 | 6800 | 10000 | 17000 | 32000 | 77000 | 150000 | 2600000 |
|---|---|---|---|---|---|---|---|---|---|
| Concentration of TOC (ppm) | 0.5 | 0.5 | 1.0 | 1.0 | 2.0 | 2.0 | 4.0 | 10.0 | 40.0 |
| Actual concentration after deducting the baseline (ppm) | 0.493 | 0.498 | 0.991 | 0.997 | 1.999 | 1.998 | 4.000 | 10.000 | 40.000 |
| Retention time (min) | 41.52 | 23.69 | 23.33 | 23.01 | 22.81 | 22.28 | 21.41 | 20.55 | 16.45 |

Using bovine serum albumin as the DON concentration test sample, the results are as follows:

Detection of the concentration of organic carbon: the detection range of the concentration of organic carbon provided by the present invention is 0.03 µg/L to 50 mg/L;

Detection of organic nitrogen concentration: when the optical detection path of the ultraviolet detector is 10 mm, the present invention's method measures the organic nitrogen concentration in a range of 0.12 mg/L to 10 mg/L.

The above description of the embodiments is to facilitate ordinary skill in the technical field to understand and use the invention. Those skilled in the art can easily modify these embodiments and apply the general principles described here to other embodiments without creative work. Therefore, the present invention is not limited to the embodiments mentioned above. The improvements and modifications made by those skilled in the art based on the disclosure of the present invention without departing from the present invention's scope should fall within the protection scope of the present invention.

What is claimed is:

1. An instrument for simultaneously testing a molecular weight distribution and an organic nitrogen of water samples, comprising a tail-end injection valve, a chromatographic column, a pressure relief valve, an acid-adding injection valve, an oxygen-adding injection valve, an helical tube for an acid-oxygen reaction, a carbon dioxide ($CO_2$) remover, a ultraviolet digester, a second gas-water separation membrane, a buffer solution injection valve, a helical tube for a buffer solution reaction, a cadmium column, a chromogenic agent injection valve, a helical tube for a chromogenic agent reaction and a ultraviolet detector, sequentially connected via a pipeline, the tail-end injection valve is configured to receive a fluid phase and a sample, the second gas-water separation membrane is connected to an electrical conductivity-based $CO_2$ detector, the ultraviolet detector and the electrical conductivity-based $CO_2$ detector are both connected to a data processing computer.

2. The instrument for simultaneously testing the molecular weight distribution and the organic nitrogen of the water samples according to claim 1, wherein the tail-end injection valve is connected with a sampling pump and a sample bottle, and the tail-end injection valve is further connected with a fluid phase infusion pump and a fluid phase reagent bottle,
the acid-adding injection valve is connected with an acid injection pump and an acid bottle,
the oxygen-adding injection valve is connected with an oxygen liquid injection pump and an oxygen liquid bottle,
the buffer solution injection valve is connected with a buffer solution injection pump and a buffer solution reagent bottle,
the chromogenic agent injection valve is connected with a chromogenic agent injection pump and a chromogenic agent reagent bottle.

3. The instrument for simultaneously testing the molecular weight distribution and the organic nitrogen of the water samples according to claim 1, wherein the $CO_2$ remover comprises a first gas-water separation membrane, a gas collecting coil, a purge pump and a diaphragm, the first gas-water separation membrane, the gas collecting coil and the diaphragm are connected in sequence, and the first gas-water separation membrane is connected to an acid-oxygen reaction spiral pipe through a pipeline, the diaphragm is connected with the ultraviolet digester (16) through a pipeline, the blow-off pump is connected to the gas collecting coil.

4. The instrument for simultaneously testing the molecular weight distribution and the organic nitrogen of the water samples according to claim 3, wherein the ultraviolet digester comprises a heating wire, a transparent quartz spiral tube and an ultraviolet lamp, the transparent quartz spiral tube is connected between the diaphragm and the second gas-water separation membrane through a pipeline, the ultraviolet lamp is located above the transparent quartz spiral tube (30), the heating wire is located under the transparent quartz spiral tube.

5. The instrument for simultaneously testing the molecular weight distribution and the organic nitrogen of the water samples according to claim 1, wherein the electrical conductivity-based $CO_2$ detector comprises an ultra-pure water tank and an ultra-pure water pump and a conductivity cell, which are connected in sequence, the sample oxidized by the ultraviolet digester passes through a gas-water separation membrane, the $CO_2$ separates and dissolves in ultra-pure water driven by the ultra-pure water pump and purifies by ion purification resin, then passes into the conductivity cell, the amount of $CO_2$ is measured by detecting the change of liquid conductivity in the conductivity cell, and a specific conversion relationship characterizes a concentration of TOC.

6. A method of using the instrument for simultaneously testing the molecular weight distribution and the organic nitrogen of the water samples according to claim 1, comprising the following steps:
a sample is collected into a pipeline, mixed with a fluid phase, and then separated by a chromatographic column, components of the sample flow out in sequence according to a different molecular weight, and then a pressure is reduced by a pressure relief valve, the different molecular weight of the components of the separated sample pass through an acid-adding injection valve and an oxygen-adding injection valve, injecting an acid liquor into the acid-adding injection valve, injecting an oxygen liquor into the oxygen-adding injection valve, and fully reacting the components to be detected, the fluid phase, the acid liquor and the oxygen liquor in an acid-oxygen reaction spiral tube;
inorganic carbon in the components to be detected is acidified by the acid liquor to produce $CO_2$, which is blown off into the air through the back remover of $CO_2$;
the components to be detected removed from inorganic carbon reach in a ultraviolet digester through a pipeline, TOC of the components is oxidized to $CO_2$ and DON is oxidized to nitrate nitrogen, the oxidized sample passes through a gas-liquid separation membrane to separate the generated $CO_2$ into an electrical conductivity-based $CO_2$ detector, the electrical conductivity-based CO2 detector detects an amount of $CO_2$, and a specific conversion relationship characterizes a concentration of TOC, after that, the remaining components without TOC are added to a buffer solution through a buffer solution injection valve, then after a reduction of a cadmium column, nitrate nitrogen is reduced to nitrite nitrogen, then a reagent is added through a chromogenic agent injection valve, and a mixing reaction is carried out in a helical tube for a chromogenic agent reaction, finally as an amount of nitrate-nitrogen is detected at 540 nm in a UV detector and a specific conversion relationship characterizes a concentration of DON.

7. The method according to claim 6, wherein the fluid phase is selected as phosphate buffer solution, a ionic strength is 0.1-0.4 M, a pH value is 6.8±0.2, a flow rate of a fluid phase infusion pump is selected to be 0.4-1.0 mL/min, a pressure of the fluid phase infusion pump is selected to be 1.8±0.2 MPa, a maintaining temperature of a chromatographic column is 30-60° C., a pressure is 1.8±0.2 MPa before the chromatographic column, a pressure after the chromatographic column passes through a pressure relief valve is 1 bar, a flow state is free flow, in the ultraviolet digester, a wavelength of a UV lamp is 190 nm, and a heating temperature is set to be 95±2° C.

8. The method according to claim 6, wherein the sampling pump adopts a microinjection pump, a pump's working pressure is higher than 1500 psi, and a highest precision is less than 0.1%, a sampling volume is 50-500 μL, an acid injection pump and an oxygen liquid injection pump adopt the microinjection pump, a working pressure is higher than 1500 psi, a highest precision is less than 0.1% and pulse-free transportation, a flow rate of the acid oxygen injection pump and the oxygen liquid injection pump is 1.0-4.0 μL/min, and a flow rate of a chromogenic agent injection pump is 1.0-4.0 μL/min.

9. The method according to claim 6, wherein a tail-end injection valve, the acid-adding injection valve, the oxygen-adding injection valve, the buffer solution injection valve, and the chromogenic agent injection valve are all stable to add one liquid to another liquid slowly and stably for mixing without having a back suction.

10. The method according to claim 6, wherein the acid-oxygen reaction spiral tube, a helical tube for a buffer solution reaction and a chromogenic agent reaction spiral tube are all made of stainless steel PEEK tubes in a spiral manner, and the stainless steel PEEK tubes are selected as the sample pipelines in the instrument.

\* \* \* \* \*